US007799343B2

(12) United States Patent
Loughner

(10) Patent No.: US 7,799,343 B2
(45) Date of Patent: Sep. 21, 2010

(54) SAFER CONTROL OF BROADLEAF WEEDS IN TURF WITH GRANULAR FORMULATIONS OF ALS INHIBITING HERBICIDES

(75) Inventor: Daniel Louis Loughner, Huntingdon Valley, PA (US)

(73) Assignee: Dow AgroSciences LLC, Indianapolis, IN (US)

( * ) Notice: Subject to any disclaimer, the term of this patent is extended or adjusted under 35 U.S.C. 154(b) by 695 days.

(21) Appl. No.: 11/351,765

(22) Filed: Feb. 10, 2006

(65) Prior Publication Data

US 2006/0183638 A1    Aug. 17, 2006

(51) Int. Cl.
*A61K 9/14* (2006.01)
(52) U.S. Cl. .................................................. 424/489
(58) Field of Classification Search ............... 504/116.1; 424/489; 71/1
See application file for complete search history.

(56) References Cited

U.S. PATENT DOCUMENTS 5,665,673 A * 9/1997 Anderson et al. ........... 504/130

FOREIGN PATENT DOCUMENTS

WO    WO 2004/023876    3/2004

WO    PCT/US2006/004792    3/2007

OTHER PUBLICATIONS

University of GA Coop Ext Service, Postemergence of Broadleaf Weed Control with Penoxsulam in Bermudagrass (Apr. 9, 2004).*
University of GA Coop Ext Service, Tolerance of 'Ky 31' Tall Fescue to Penoxsulam (Jul. 8, 2004).*
Cooper, R. J. et al; XP0002421735 "Crabgrass control and turfgrass injury resulting from pre- and postemergent herbicides;"Database CA [Online]; Database Accession No. 1980/175674 & Proceedings of the Annual Meeting of the Northeastern Weed Science Society 34, 347-52 CODEN: PNWSBF; ISSN: 0078-1703, 1980; Chemical Abstracts Service, Columbus, Ohio.
Davis, H.E. et al; XP002421736 "Granular dicot weed control and fertilizer interactions in turfgrass;" Database accession No. 1981:134000 & Proceedings of the Annual Meeting of the Northeastern Weed Science Society 35, 280-4 CODEN: PNWSBF; ISSN: 0078-1703, 1981; Chemical Abstracts Service, Columbus, Ohio.
XP002421772; Database WPI Week 199953; Oct. 5, 1999; Derwent Publications Ltd. London, GB.

* cited by examiner

*Primary Examiner*—Alton N Pryor
(74) *Attorney, Agent, or Firm*—Craig E. Mixan

(57) ABSTRACT

The harmful effects of ALS inhibiting herbicides on turfgrass are reduced by applying the herbicides as solid granular compositions, particularly on solid granular fertilizer compositions.

7 Claims, No Drawings

SAFER CONTROL OF BROADLEAF WEEDS IN TURF WITH GRANULAR FORMULATIONS OF ALS INHIBITING HERBICIDES

BACKGROUND OF THE INVENTION

This invention relates to a method of controlling broadleaf weeds in turf using an herbicidally effective amount of an acetolactate synthase (ALS) inhibiting herbicide. More particularly, when applied as a solid granular formulation, ALS inhibiting herbicides are safer to desirable turf species.

The search for compounds which have a combination of excellent herbicidal activity towards target weeds and low toxicity towards non-target plants is a continuing one because of factors such as the desire for compounds exhibiting greater activity, better selectivity, lower undesirable environmental impact, lack of phytotoxicity to the locus of application, lower production and market cost and higher effectiveness against weeds resistant to known herbicides. In particular, there exists a need for effective control of broadleaf weeds in turfgrass. Commercial herbicides, for example, 2,4-D, mecoprop-P, clopyralid, triclopyr and methylarsonic acid, have serious deficiencies such as requiring a high application rate to be effective, possessing less than desirable environmental profiles, having too great or too poor soil mobility and/or being toxic to non-target plants and or turfgrass species.

Herbicides that inhibit acetolactate synthase (ALS) have recently been found to effectively control broadleaf weeds in turfgrass at relatively low application rates; however, even at the low doses required to control the broadleaf weeds, some stress is often observed in many non-target turfgrass species. It would be desirable to have a method for making the ALS inhibiting herbicides less phytotoxic to the turfgrass without substantially affecting there control of broadleaf weeds.

SUMMARY OF THE INVENTION

It has now been found that the harmful effects of ALS inhibiting herbicides on turfgrass are reduced by applying the herbicides as solid granular compositions. The invention concerns a method for protecting turfgrass from the harmful effects of ALS inhibiting herbicides comprising the step of treating the turfgrass or the locus thereof with a dry solid granular herbicidal composition comprising an herbicidally effective amount of the ALS inhibiting herbicide in admixture with an agriculturally acceptable adjuvant or carrier. Particularly effective compositions are comprised of (a) an herbicidally effective amount of the ALS inhibiting herbicide in admixture with an agriculturally acceptable adjuvant or carrier and (b) a fertilizer.

DETAILED DESCRIPTION OF THE INVENTION

Several classes of herbicides have been identified as owing their activity to their ability to inhibit the plant enzyme acetolactate synthase (ALS), which is essential for the synthesis of branched-chain amino acids valine, leucine, and isoleucine. Inhibition of amino acid production subsequently inhibits cell division. Among the classes of herbicides having this mode of action are: imidazolinone herbicides such as imazamethabenz, imazamox, imazapic, imazapyr, imazaquin and imazethapyr; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulftiron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; triazolopyrimidine herbicides such as cloransulam, diclosulam, florasulam, flumetsulam, metosulam, penoxsulam and N-(5,7-dimethoxy[1,2,4]triazolo[1,5-a]pyrimidin-2-yl)-2-methoxy-4-(trifluoromethyl)-3-pyridine-sulfonamide; and pyrimidinyloxybenzoic acid herbicides such as bispyribac and pyriminobac. These herbicides are described in *The Pesticide Manual*, 13$^{th}$ Ed.

The ALS inhibiting herbicides are useful in controlling broadleaf weeds and sedges in turfgrass. They are particularly effective against most important weeds in this application, viz., white clover, *Trifolium repens* L. (TRFRE); buckhorn plantain, *Plantago lanceolata* L. (PLALA); dandelion, *Taraxacum officinale* (TAROF); broadleaf plantain, *Plantago major* L. (PLAMA); ground ivy, *Glechoma hederacea* L. (GLEHE); common lespedeza, *Lespedeza striata* (LESST); pennywort (dollarweed), *Hydrocotyle* spp (HYDSS); Virginia buttonweed, *Diodia virginiana* L. (DIQVI) English daisy, *Bellis perennis* L. (BELPE); annual bluegrass, *Poa annua* (POANN); and yellow nutsedge, *Cypres esculentus* L. (CYPES).

At rates herbicidally effective against these weeds, the ALS inhibiting herbicides sometimes cause observable damage to Bermudagrass, creeping bentgrass, red fescue, tall fescue, perennial ryegrass, zoysiagrass, centipedegrass, St. Augustinegrass and Kentucky bluegrass. Sometimes this damage may be acceptable but oftentimes it is not.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include emerging seedlings and established vegetation.

Herbicidal activity is exhibited by ALS inhibiting herbicides when they are applied directly to the turfgrass or to the locus thereof at any stage of growth or before emergence of the broadleaf weeds. The effect observed depends upon the plant species to be controlled, the stage of growth of the plant, the particle size of solid components, the environmental conditions at the time of use, the specific adjuvants and carriers employed, the soil type, and the like, as well as the amount of chemical applied. These and other factors can be adjusted as is known in the art to promote selective herbicidal action. Generally, it is preferred to apply ALS inhibiting herbicides postemergence in turf to relatively immature undesirable vegetation to achieve the maximum control of weeds.

Application rates of about 5 to about 280 grams of active ingredient per hectare (gai/Ha) are generally employed in postemergence operations with about 20 to about 180 gai/Ha being preferred; for preemergence applications, rates of about 4 to about 140 gai/Ha are generally employed with about 9 to about 70 gai/Ha being preferred.

ALS inhibiting herbicides are often best applied in conjunction with one or more other herbicides to obtain control of a wider variety of undesirable vegetation. When used in conjunction with other herbicides, ALS inhibiting herbicides can be formulated with the other herbicide or herbicides, broadcast with the other herbicide or herbicides, or applied sequentially with the other herbicide or herbicides. Some of the herbicides that can be employed in conjunction with ALS inhibiting herbicides include 2,4-D, 2,4-DP, 2,4-DB, acetochlor, aciflurofen, aclonifen, alachlor, aminopyralid, ametryn, aminotriazole, ammonium thiocyanate, asulam, atrazine, benefin, benfluralin, bensulide, Bentazon, bifenox, bromacil, bromoxynil, butafenacil, butralin, carbetamide, carfentrazone, clethodim, chlorflurenol, clopyralid, clomazone, cycloxydim, DCPA, dicamba, dichlobenil, diclofop, diclosulam, dithiopyr, dichlorprop-P, diflufenican, diflufenzopyr, diquat, diuron, DSMA, endothal-disodium, ethoxysulfuron, EPTC, ET-751, ethofumesate, flazasulfuron, florasulam, flucetosulfuron, flufenacet, DE-742, flupoxam, fluazifop, fluazifop-P-butyl, flumioxazin, foramsulfuron, fluroxypyr, glufosinate, glufosinate-ammonium, glyphosate, haloxyfop-methyl, halosulfuron, hexazinone, ioxynil, indanofan, isoproturon, isoxaben, isoxaflutole, kerbutilate, KIH-485, lenacil, MCPA, mecoprop-P, MCPP, MSMA, mesotrione, metolachlor, metribuzin, napropamide, norflurazon, orthobencarb, oryzalin, oxadiargyl, oxadiazon, oxaziclomefone, oxyfluorfen, paraquat, pebulate, pendimethalin, picolinafen, picloram, pinoxaden, profluazol, propoxycarbazone, propyzamide, prosulfocarb, prodiamine, pyrithiobac, pyributicarb, pyrazasulfuron-ethyl, pyraflufen-ethyl, pyrimisulfan, quinclorac, quizalofop-ethyl-D, sethoxydim, siduron, simazine, sulfentrazone, sulfosate, sulfometuron, sulfosulfuron, tebuthiuron, terbacil, thenylchlor, thiazopyr, topramezone, tralkoxydim, triclopyr and trifluralin, triaziflam, tritosulfuron and trifloxysulfuron-sodium. It is generally preferred to apply ALS inhibiting herbicides and other complementary herbicides at the same time. When applying in this way synergistic responses have been observed specific to species, and mixture.

ALS inhibiting herbicides can also be applied with herbicide safeners such as benoxacor, benthiocarb, cloquintocet, cyometrinil, daimuron, dichlormid, dicyclonon, fenchlorazole-ethyl, fenclorim, flurazole, fluxofenim, furilazole, isoxadifen-ethyl, mefenpyr-diethyl, MG191, MON4660, oxabetrinil, R29148 and N-phenylsulfonylbenzoic acid amides.

While it is possible to utilize the ALS inhibiting herbicide directly, it is preferable to use it in mixtures containing a herbicidally effective amount of the ALS inhibiting herbicide along with at least one agriculturally acceptable adjuvant or carrier. Suitable adjuvants or carriers should not react chemically with ALS inhibiting herbicides or other composition ingredients. Such mixtures can be designed for application directly to weeds or their locus Suitable agricultural adjuvants and carriers that are useful in preparing the herbicidal mixtures of the invention are well known to those skilled in the art.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, granule fertilizer and the like.

The composition may contain one or more surface-active agents. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

The compositions may also contain other compatible components, for example, other herbicides, plant growth regulants, fungicides, insecticides, and the like and can be formulated with solid, particulate fertilizer carriers such as ammonium nitrate, urea and the like that are used to deliver nutrients to turfgrass.

Nitrogen based fertilizers are routinely used in turfgrass management to feed grass and stimulate growth. ALS inhibiting herbicides are preferably delivered on a granule fertilizer or one that contains nitrogen, phosphorus or potassium. These ALS inhibiting herbicide formulations were less injurious than liquid applications of ALS inhibiting herbicides. Such a granule is prepared by spraying an aqueous suspension of pulverized ALS inhibiting herbicide onto a bed of fertilizer granules, under efficient flowing conditions. A solution of ALS inhibiting herbicide in an organic solvent may be used as alternative spray liquor. The water or the organic solvent used as diluent may be removed by heating and/or vacuum drying, if desired. If the granule gets sticky due to residual moisture, a small amount of absorbent, such as amorphous silica, may be added to keep granule free-flowing.

The concentration of ALS inhibiting herbicide in the herbicidal compositions of this invention is generally from about 0.001 to about 98 percent by weight. Concentrations from about 0.01 to about 90 percent by weight are often employed.

The present compositions can be applied to weeds or their locus by the use of conventional ground or aerial dusters and granule applicators and by other conventional means known to those skilled in the art.

The following Examples are presented to illustrate the various aspects of this invention and should not be construed as limitations to the claims.

EXAMPLES

Preparation of Penoxsulam Fertilizer Granules

A 50% aqueous suspension concentrate of penoxsulam was at first prepared: Penoxsulam was dispersed in water, in the presence of surfactants and other inert ingredients, and pulverized by means of bead-milling until an average particle size of 2 to 5 micrometer was achieved. The milled concentrate was diluted with water and sprayed on to a bed of fertilizer granules in a tumbler to obtain a final formulation product.

Example 1

Penoxsulam 0.06% 0-0-6 Potash Granule

In a tumbler, 3,984.7 grams of 0-0-6 potash granule of average particle size of 1.5 mm was weighed in. Tumbler was run at a speed that enabled a good flow of the granule. In an atomizer, 5.28 grams of the 50% penoxsulam milled concentrate (2.64 grams penoxsulam) and 10.0 grams of water were added. The diluted suspension of penoxsulam was sprayed onto the granule. The obtained granule was assayed and found to contain 0.064% penoxsulam.

Example 2

Bispyribac-Sodium 0.065% 0-0-6 Potash Granule

Following the same preparation method as described in Example 1, bispyribac-sodium 0.065% granule was prepared from 3,988.4 grams of 0-0-6 potash granule of average particle size of 1.5 mm, 3.58 grams of Regiments (2.86 grams bispyribac-sodium), and 8.0 grams of water. The obtained granule was found to contain 0.069% bispyribac-sodium.

Example 3

Trifloxysulfuron-Sodium 0.016% 0-0-6 Potash Granule

Following the same preparation method as described in Example 1, trifloxysulfuron-sodium 0.016% granule was prepared from 3,991.1 grams of 0-0-6 potash granule of average particle size of 1.5 mm, 0.94 grams of Monument® WG (0.71 grams trifloxysulfuron-sodium), and 8.0 grams of water. The obtained granule was found to contain 0.020% trifloxysulfuron-sodium.

Example 4

Metsulfuron-Methyl 0.009% 0-0-6 Potash Granule

Following the same preparation method as described in Example 1, metsulfuron-methyl 0.009% granule was prepared from 3,991.3 grams of 0-0-6 potash granule of average particle size of 1.5 mm, 0.66 grams of Ally® (0.40 grams metsulfuron-methyl), and 8.0 grams of water. The obtained granule was found to contain 0.0090% metsulfuron-sodium.

Example 5

Imazaquin 0.375% 0-0-6 Potash Granule

In a tumbler, 3,966.4 grams of 0-0-6 potash granule of average particle size of 1.5 mm was weighed in. Tumbler was run at a speed that enabled a good flow of the granules. In an atomizer, 23.6 grams of Sceptor® 70DG (16.5 grams imazaquin) and 50.0 grams of water were added. The diluted suspension of Sceptor was sprayed onto the granules. The granule was put in a dryer set at 50° C. overnight to remove excess (40 grams) water. The obtained granule was found to contain 0.37% imazaquin.

Improved Turf Tolerance with Granule Herbicides

Turf tolerance studies were conducted in monoculture stands of perennial ryegrass and tall fescue. Replicated trials, containing a minimum of three replications and having individual plots ranging in size from 25 to 50 ft. sq (2.3 to 4.6 square meters), were initiated in the late spring when turf was actively growing. Granule treatments were uniformly applied to individual plots using a common hand-shaker method. Natural rainfall and supplemental irrigation, fertilizer, fungicides and insecticides were used to maintain healthy turf throughout the study period. Turf tolerance evaluations were made weekly for 8 weeks after application. Evaluations compared treated and untreated plot areas and consisted of one or all of the following evaluations: 1) visual estimate of turf injury made on a 0 to 10 scale with 0 indicating no visible injury symptoms, 10 being dead turf and 3 or less being commercially acceptable; 2) visual estimate of turf color made on a 0 to 10 scale with 0 being brown to dead turf, 10 being a lush green turf of highest quality and 6.5 being commercially acceptable; 3) visual estimate of turf density made on a 0 to 100 scale with 0 being bare ground, 100 being a thick solid stand of highest quality and 90 percent density being commercially acceptable; 4) visual estimate of turf quality made on a 0 to 10 scale with 0 being brown to dead turf, 10 being a lush green turf of highest quality and 6.5 being commercially acceptable.

Treatments evaluated, application rate employed, turf species evaluated and results are presented in the following Tables I-III.

TABLE I

Tall Fescue Tolerance to ALS Herbicides: Indiana 2004 14 Days After Treatment Evaluation

| Herbicide | g ai/Ha | Formulation | Injury (0-10 Scale) | Color (0-10 Scale) | Cover (0-100 Scale) |
|---|---|---|---|---|---|
| Penoxsulam | 35 | Liquid | 3.0 h-k[1] | 7.8 abc | 92.5 ab |
| | | Granule | 0.3 m | 9.0 a | 100.0 a |
| Imazaquin | 104 | Liquid | 5.3 d-g | 5.3 g | 70.0 cde |
| | | Granule | 0.5 lm | 9.0 a | 100.0 a |
| Bispyribac-sodium | 75 | Liquid | 2.0 j-m | 8.8 a | 97.5 a |
| | | Granule | 0.0 m | 9.0 a | 100.0 a |
| Trifloxysulfuron-sodium | 9.2 | Liquid | 8.0 ab | 3.8 h | 51.3 f |
| | | Granule | 5.8 c-f | 5.8 efg | 70.0 cde |
| Metsulfuron-methyl | 10.4 | Liquid | 4.3 e-l | 6.8 c-f | 87.5 ab |
| | | Granule | 0.8 lm | 8.8 a | 100.0 a |

[1]Means followed by same letter do not significantly differ (P = .05, Duncan's New MRT)

TABLE II

Perennial Ryegrass Tolerance to ALS Herbicides: Indiana 2004 21 Days After Treatment Evaluation

| Herbicide | g ai/Ha | Formulation | Injury (0-10 Scale) | Color (0-10 Scale) | Cover (0-100 Scale) |
|---|---|---|---|---|---|
| Penoxsulam | 35 | Liquid | 4.3 d-g[1] | 6.5 def | 87.5 a-d |
| | | Granule | 1.5 i-l | 8.3 abc | 100.0 a |
| Imazaquin | 104 | Liquid | 3.3 e-l | 8.3 abc | 97.5 ab |
| | | Granule | 1.8 h-l | 8.8 ab | 98.8 a |

TABLE II-continued

Perennial Ryegrass Tolerance to ALS Herbicides:
Indiana 2004 21 Days After Treatment Evaluation

| Herbicide | g ai/Ha | Formulation | Injury (0-10 Scale) | Color (0-10 Scale) | Cover (0-100 Scale) |
|---|---|---|---|---|---|
| Bispyribac-sodium | 75 | Liquid | 4.5 c-f | 6.5 def | 85.0 a-d |
|  |  | Granule | 1.0 jkl | 8.5 ab | 100.0 a |
| Trifloxysulfuron-sodium | 9.2 | Liquid | 8.0 ab | 4.0 g | 57.5 f |
|  |  | Granule | 5.3 cde | 6.8 c-f | 87.5 a-d |
| Metsulfuron-methyl | 10.4 | Liquid | 6.0 cd | 6.0 ef | 67.5 ef |
|  |  | Granule | 4.5 c-f | 6.5 def | 82.5 bcd |

[1]Means followed by same letter do not significantly differ (P = .05, Duncan's New MRT)

TABLE III

Perennial Ryegrass Turf Quality ALS Herbicides: Pennsylvania 2004

| Herbicide | g ai/Ha | Formulation | 4 DAA[1] | 16 DAA | 36 DAA |
|---|---|---|---|---|---|
| Penoxsulam | 35 | Liquid | 9.3 ab[2] | 7.0 cde | 10.0 a |
|  |  | Granule | 9.7 a | 8.0 bcd | 10.0 a |
| Imazaquin | 104 | Liquid | 7.7 cd | 3.3 ij | 7.7 a |
|  |  | Granule | 10.0 a | 3.0 j | 3.3 bc |
| Bispyribac-sodium | 75 | Liquid | 8.0 bcd | 5.7 e-h | 10.0 a |
|  |  | Granule | 8.7 abc | 7.3 b-e | 10.0 a |
| Trifloxysulfuron-sodium | 9.2 | Liquid | 7.7 cd | 2.7 j | 1.3 cd |
|  |  | Granule | 9.3 ab | 4.3 g-j | 8.3 a |
| Metsulfuron-methyl | 10.4 | Liquid | 8.7 abc | 4.3 g-j | 8.3 a |
|  |  | Granule | 10.0 a | 5.0 f-l | 8.3 a |

[1]DAA = Days After Application
[2]Means followed by same letter do not significantly differ (P = .05, Duncan's New MRT)

Postemergent Activity of Granule Herbicides

Field studies were conducted in established turfgrass sites containing a natural population of target broadleaf weeds. Replicated trials, containing a minimum of three replications and having individual plots ranging in size from 25 to 50 ft. sq (2.3 to 4.6 square meters), were initiated in the late spring when turf and weeds were actively growing. Granule treatments were uniformly applied to individual plots using a common hand-shaker method. Applications were made in the early morning when dew was present. Natural rainfall and supplemental irrigation were used to maintain healthy turf and active weed growth throughout the study period. Control of each weed species in the study site was made at approximately 2, 4 and 8 weeks after treatment. Control was determined visually by comparing treated and untreated weeds and scored on a 0 to 100 percent scale where 0 corresponds to no control and 100 corresponds to complete kill.

Treatments evaluated, application rate employed, weed species evaluated and results are presented in the following Tables IV-V.

TABLE IV

Percent Weed Control ALS Herbicides: Pennsylvania 2004

| Herbicide | g ai/Ha | Formulation | TAROF 29DAA[1] | TAROF 56DAA | TRFRE 29DAA | TRFRE 56DAA |
|---|---|---|---|---|---|---|
| Penoxsulam | 35 | Liquid | 44.4 a-d[2] | 11.1 ef | 100.0 a | 98.7 a |
|  |  | Granule | 57.8 abc | 34.4 c-f | 98.3 ab | 83.9 abc |
| Imazaquin | 104 | Liquid | 58.9 abc | 11.1 ef | 22.2 c-f | 11.1 fg |
|  |  | Granule | 13.9 b-e | 17.8 ef | 0.0 ef | 23.3 efg |
| Bispyribac-sodium | 75 | Liquid | 95.7 a | 57.1 a-e | 88.9 abc | 55.6 b-e |
|  |  | Granule | 45.0 a-d | 23.3 def | 36.1 a-e | 36.a d-g |
| Trifloxysulfuron-sodium | 9.2 | Liquid | 98.3 a | 100.0 a | 100.0 a | 100.0 a |
|  |  | Granule | 80.6 a | 40.0 b-f | 80.0 abc | 56.7 a-e |
| Metsulfuron-methyl | 10.4 | Liquid | 99.1 a | 97.4 a | 95.8 ab | 100.0 a |
|  |  | Granule | 87.2 a | 67.2 a-d | 93.9 ab | 93.9 ab |

[1]DAA = Days After Application
[2]Means followed by same letter do not significantly differ (P = .05, Duncan's New MRT)

TABLE V

Percent Weed Control ALS Herbicides: Pennsylvania 2004

| Herbicide | g ai/Ha | Formulation | PLALA 29DAA[1] | PLALA 56DAA | POANN 29DAA | POANN 56DAA |
|---|---|---|---|---|---|---|
| Penoxsulam | 35 | Liquid | 41.7 a-d[2] | 70.6 a-f | 4.4 efg | 31.1 c-g |
| | | Granule | 73.3 abc | 43.3 c-h | 0.0 g | 13.7 efg |
| Imazaquin | 104 | Liquid | 16.7 a-f | 8.3 gh | 8.8 efg | 26.2 d-g |
| | | Granule | 22.2 a-f | 41.1 c-h | 31.4 c-g | 18.1 efg |
| Bispyribac-sodium | 75 | Liquid | 75.6 abc | 57.8 a-g | 28.3 d-g | 23.3 d-g |
| | | Granule | 27.8 a-e | 27.8 d-h | 40.0 c-g | 28.9 d-g |
| Trifloxysulfuron-sodium | 9.2 | Liquid | 0.0 fg | 33.3 c-h | 95.4 a | 77.2 ab |
| | | Granule | 0.0 fg | 11.1 gh | 34.5 c-g | 39.9 cde |
| Metsulfuron-methyl | 10.4 | Liquid | 97.7 a | 78.9 a-d | 39.2 c-g | 17.5 efg |
| | | Granule | 58.3 a-d | 85.0 abc | 32.2 c-g | 31.1 c-g |

[1]DAA = Days After Application
[2]Means followed by same letter do not significantly differ (P = .05, Duncan's New MRT)

What is claimed is:

1. A method for protecting turfgrass from the harmful effects of ALS inhibiting herbicides comprising the step of treating the turfgrass or the locus thereof with a dry solid granular herbicidal composition comprising an herbicidally effective amount of the ALS inhibiting herbicide in admixture with an agriculturally acceptable adjuvant or carrier.

2. A method of claim 1 in which the dry solid granular herbicidal composition comprises (a) an herbicidally effective amount of the ALS inhibiting herbicide in admixture with an agriculturally acceptable adjuvant or carrier and (b) a fertilizer.

3. A method of claim 1 or claim 2 in which the ALS inhibiting herbicide is an imidazolinone herbicide such as imazamethabenz, imazamox, imazapic, imazapyr, imazaquin and imazethapyr.

4. A method of claim 1 or claim 2 in which the ALS inhibiting herbicide is a pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron.

5. A method of claim 1 or claim 2 in which the ALS inhibiting herbicide is a triazinylsulfonylurea herbicide such as chlorsulfuron, cinosulfuron, ethametsulfuron, iodosulfuron, metsulfuron, prosulfuron, thifensulfuron, triasulfuron, tribenuron, triflusulfuron and tritosulfuron.

6. A method of claim 1 in which the ALS inhibiting herbicide is a triazolopyrimidine herbicide such as cloransulam, diclosulam, florasulam, flumetsulam, metosulam, penoxsulam and N-(5,7-dimethoxy-[1,2,4]triazolo[1,5-a]pyrimidin-2-yl)-2-methoxy-4-(trifluoromethyl)-3-pyridinesulfonamide.

7. A method of claim 1 or claim 2 in which the ALS inhibiting herbicide is a pyrimidinyloxybenzoic acid herbicide such as bispyribac and pyriminobac.

* * * * *